United States Patent [19]

Flaugh et al.

[11] 4,087,444
[45] May 2, 1978

[54] AMIDES AS OVULATION INHIBITORS

[75] Inventors: Michael E. Flaugh; James A. Clemens, both of Indianapolis, Ind.

[73] Assignee: Eli Lilly and Company, Indianapolis, Ind.

[21] Appl. No.: 720,311

[22] Filed: Sep. 8, 1976

[51] Int. Cl.² .......................................... C07D 209/18
[52] U.S. Cl. ................... 260/326.13 B; 260/326.13 R; 260/326.15; 260/326.16; 260/570.8 R; 260/590 D; 260/590 R; 260/592; 424/274
[58] Field of Search ............................... 260/326.13 R

[56] References Cited

U.S. PATENT DOCUMENTS 3,925,382  12/1975  Ishigumi et al. ........ 260/326.13 R X

FOREIGN PATENT DOCUMENTS 445,661  6/1975  U.S.S.R. ...................... 260/326.13 R

OTHER PUBLICATIONS

Chem. Abstract, 63:p18034c.

*Primary Examiner*—Ethel G. Love
*Attorney, Agent, or Firm*—William C. Martens, Jr.; Arthur R. Whale

[57] ABSTRACT

N-[2-(5-methoxy-6-haloindol-3-yl)ethyl]amides are valuable, orally active, ovulation inhibitors.

25 Claims, No Drawings

AMIDES AS OVULATION INHIBITORS

CROSS REFERENCE

This application is a continuation-in-part of Application Ser. No. 626,890, filed Oct. 29, 1975, now abandoned.

BACKGROUND OF THE INVENTION

Melatonin (N-acetyl-5-methoxytryptamine) is a natural product isolated from the pineal glands of beef cattle. It is reported by Ying and Greep, Endocrinology, 92 (1), 333–5 (1973), that melatonin has an inhibitory effect on ovulation in cyclic rodents. This inhibitory effect is realized when melatonin is administered intracardially in relatively large doses during the critical period of proestrus. However, when melatonin is administered orally, its inhibitory effect on ovulation is substantially diminished over that available by intracardial administration. It now has been discovered that a particular class of tryptamines, N-acyl-5-methoxy-6-halotryptamines, exhibit a high level of activity as ovulation inhibitor even when administered orally.

SUMMARY OF THE INVENTION

The present invention provides novel compounds of the formula

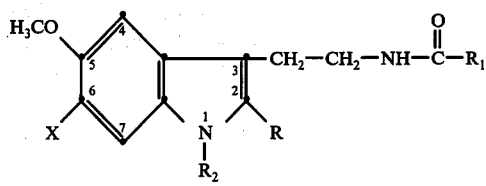

in which
R is hydrogen, $C_1$–$C_4$ alkyl, phenyl, or phenyl substituted with halo, $C_1$–$C_4$ alkyl or $C_1$–$C_4$ alkoxy;
$R_1$ is hydrogen or $C_1$–$C_4$ alkyl;
$R_2$ is hydrogen, haloacetyl, $C_1$–$C_5$ alkanoyl, benzoyl, or benzoyl substituted with halo or methyl; and
X is halogen.

Compounds of formula I are orally active as inhibitors of ovulation in mammals.

Preferred compounds of formula I are those in which $R_2$ is hydrogen.

Another preferred class of compounds of formula I are those in which $R_2$ is haloacetyl, $C_1$–$C_5$ alkanoyl, benzoyl, or benzoyl substituted with halo or methyl.

DETAILED DESCRIPTION OF THE INVENTION

The compounds prescribed by the present invention are as defined above. In the definition of the compounds of this invention, the term "$C_1$–$C_4$ alkyl" is employed. By this term is meant any of the following groups: methyl, ethyl, isopropyl, n-propyl, n-butyl, isobutyl, sec-butyl, and t-butyl.

The term "$C_1$–$C_4$ alkoxy" also is employed herein and includes methoxy, ethoxy, n-propoxy, isopropoxy, n-butoxy, isobutoxy, sec-butoxy, and t-butoxy.

The terms "halo" and "halogen" where used herein include chloro, bromo, iodo, and fluoro, and, preferably, chloro.

When, in the above definition, the term R represents a substituted phenyl group, examples of such a group include, for example, 4-chlorophenyl, 2-fluorophenyl, 3-iodophenyl, 4-bromophenyl, 3,4-dibromophenyl, 4-methylphenyl, 2-ethylphenyl, 3-n-propylphenyl, 4-isopropylphenyl, 4-n-butylphenyl, 3-t-butylphenyl, 4-sec-butylphenyl, 3,4-dimethylphenyl, 4-methoxyphenyl, 3-ethoxyphenyl, 2-n-propylphenyl, 4-isopropoxyphenyl, 3-isobutoxyphenyl, 4-t-butoxyphenyl, 3-ethoxy-4-methoxyphenyl, and the like.

The term "haloacetyl" as used herein in definition of the group $R_2$ refers to chloroacetyl, bromoacetyl, fluoroacetyl, and iodoacetyl.

The term "$C_1$–$C_5$ alkanoyl" as used herein with reference to the group $R_2$ includes formyl, acetyl, propionyl, butyryl, α-methylpropionyl, valeryl, α-methylbutyryl, β-methylbutyryl, and pivaloyl. Preferred $C_1$–$C_5$ alkanoyl groups are acetyl and pivaloyl, and, most preferably, acetyl.

The term "benzoyl substituted with halo" used in definition of the group $R_2$ defines mono- and dihalobenzoyl groups. Specific monohalobenzoyl groups are chlorobenzoyl, bromobenzoyl, fluorobenzoyl, and iodobenzoyl. Preferably, the monohalobenzoyl group is a 4-halobenzoyl, and the preferred halo substituent is chloro.

The dihalobenzoyl groups defined by $R_2$ generally are those in which both of the halo substituents are the same, and, preferably, are those in which the halo substituents are located in the 2- and 4-positions. Typical dihalobenzoyl groups include 2,4-dichlorobenzoyl, 2,4-dibromobenzoyl, 2,4-difluorobenzoyl, and 2,4-diiodobenzoyl. The preferred group is 2,4-dichlorobenzoyl.

The term "benzoyl substituted with methyl" contemplates "methylbenzoyl", "dimethylbenzoyl", and "trimethylbenzoyl". Preferred groups include 2-methylbenzoyl, 2,6-dimethylbenzoyl, 2,4,6-trimethylbenzoyl, and the like.

Examples of the compounds of this invention include the following:
N-[2-(5-methoxy-6-chloroindol-3-yl)ethyl]acetamide;
N-[2-(5-methoxy-6-fluoroindol-3-yl)ethyl]acetamide;
N-[2-(5-methoxy-6-bromoindol-3-yl)ethyl]formamide;
N-[2-(5-methoxy-6-iodoindol-3-yl)ethyl]propionamide;
N-[2-(5-methoxy-6-chloroindol-3-yl)ethyl]-n-butyramide;
N-[2-(2-methyl-5-methoxy-6-bromoindol-3-yl)ethyl]-acetamide;
N-[2-(2-ethyl-5-methoxy-6-chloroindol-3-yl)ethyl]-acetamide;
N-[2-(2-n-propyl-5-methoxy-6-chloroindol-3-yl)-ethyl]-formamide;
N-[2-(2-n-butyl-5-methoxy-6-chloroindol-3-yl)-ethyl]-formamide;
N-[2-(2-ethyl-5-methoxy-6-iodoindol-3-yl)ethyl]-propionamide;
N-[2-(2-isopropyl-5-methoxy-6-fluoroindol-3-yl)-ethyl]-α-methylpropionamide;
N-[2-(2-phenyl-5-methoxy-6-chloroindol-3-yl)ethyl]-formamide;
N-[2-(2-phenyl-5-methoxy-6-bromoindol-3-yl)ethyl]-acetamide;
N-[2-(2-phenyl-5-methoxy-6-iodoindol-3-yl)ethyl]-propionamide;
N-[2-((2-(4-chlorophenyl)-5-methoxy-6-chloroindol-3-yl))ethyl]formamide;
N-[2-((2-(3-fluorophenyl)-5-methoxy-6-bromoindol-3-yl))ethyl]acetamide;
N-[2-((2-(2-fluorophenyl)-5-methoxy-6-chloroindol-3-yl))ethyl]propionamide;

N-[2-((2-(4-methylphenyl)-5-methoxy-6-bromoindol-3-yl))ethyl]formamide;
N-[2-((2-(3-ethylphenyl)-5-methoxy-6-fluoroindol-3-yl))ethyl]butyramide;
N-[2-((2-(4-n-propylphenyl)-5-methoxy-6-chloroindol-3-yl))ethyl]formamide;
N-[2-((2-(3-isopropylphenyl)-5-methoxy-6-fluoroindol-3-yl))ethyl]acetamide;
N-[2-((2-(4-methoxyphenyl)-5-methoxy-6-chloroindol-3-yl))ethyl]propionamide;
N-[2-((2-(3-ethoxyphenyl)-5-methoxy-6-bromoindol-3-yl))ethyl]acetamide;
N-[2-((2-(3-n-propoxyphenyl)-5-methoxy-6-fluoroindol-3-yl))ethyl]acetamide;
N-[2-((2-(4-t-butoxyphenyl)-5-methoxy-6-chloroindol-3-yl))ethyl]formamide;
N-[2-((2-(3-n-butoxyphenyl)-5-methoxy-6-chloroindol-3-yl))ethyl]acetamide;
N-[2-(1-acetyl-5-methoxy-6-chloroindol-3-yl)-ethyl]-acetamide;
N-[2-(1-propionyl-5-methoxy-6-fluoroindol-3-yl)ethyl]-acetamide;
N-[2-(1-pivaloyl-5-methoxy-6-bromoindol-3-yl)-ethyl]-formamide;
N-[2-(1-chloroacetyl-5-methoxy-6-iodoindol-3-yl(ethyl]propionamide;
N-[2-(1-bromoacetyl-5-methoxy-6-chloroindol-3-yl)ethyl]-n-butyramide;
N-[2-(1-valeryl-2-methyl-5-methoxy-6-bromoindol-3-yl)ethyl]acetamide;
N-[2-(1-butyryl-2-ethyl-5-methoxy-6-chloroindol-3-yl)ethyl]acetamide;
N-[2-(1-benzoyl-2-n-propyl-5-methoxy-6-chloroindol-3-yl)ethyl]formamide;
N-[[2-[1-(4-chlorobenzoyl)-2-n-butyl-5-methoxy-6-chloroindol-3-yl]ethyl]]formamide;
N-[[2-[1-(4-bromobenzoyl)-2-ethyl-5-methoxy-6-iodoindol-3-yl]ethyl]]propionamide;
N-[[2-[1-(2,4-dichlorobenzoyl)-2-isopropyl-5-methoxy-6-fluoroindol-3-yl]ethyl]]-α-methylpropionamide;
N-[[2-[1-(2,4-difluorobenzoyl)-2-phenyl-5-methoxy-6-chloroindol-3-yl]ethyl]]formamide;
N-[[2-[1-(4-iodobenzoyl)-2-phenyl-5-methoxy-6-bromoindol-3-yl]ethyl]]acetamide;
N-[[2-[1-(2-methylbenzoyl)-2-phenyl-5-methoxy-6-iodoindol-3-yl]ethyl]]propionamide;
N-[[2-[1-(2,6-dimethylbenzoyl)-2-(4-chlorophenyl)-5-methoxy-6-chloroindol-3-yl]ethyl]]formamide;
N[[2-[1-(2,4,6-trimethylbenzoyl)-2-(3-fluorophenyl)-5-methoxy-6-bromoindol-3-yl]ethyl]]acetamide;
N-[2-(1-pivaloyl-5-methoxy-6-chloroindol-3-yl)ethyl]-acetamide;
N-[2-(1-chloroacetyl-5-methoxy-6-chloroindol-3-yl)ethyl]acetamide;
N-[[2-[1-(4-chlorobenzoyl)-5-methoxy-6-chloroindol-3-yl]ethyl]]acetamide;
N-[[2-[1-(2,4-dichlorobenzoyl)-5-methoxy-6-chloroindol-3-yl]ethyl]]acetamide;
N-[[2-[1-(2-methylbenzoyl)-5-methoxy-6-chloroindol-3yl]ethyl]]-acetamide;
N-[[2-[1-(2,6-dimethylbenzoyl)-5-methoxy-6-chloroindol-3-yl]ethyl]]acetamide;
N-[[2-[1-(2,4,6-trimethylbenzoyl)-5-methoxy-6-chloroindol-3-yl]ethyl]]acetamide; and the like.

The compounds of the present invention are prepared by acylating a substituted tryptamine of the formula

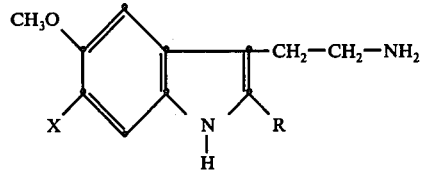

in which X and R are as aforedescribed. The acylation is accomplished by employment of conventional procedures. For example, the substituted tryptamine can be reacted with an activated form of a carboxylic acid of the formula

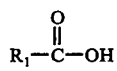

in which $R_1$ is as defined hereinabove. Suitable such activated forms include, for example, the anhydride or mixed anhydride of the carboxylic acid. Acylation also can be carried out by reacting the carboxylic acid in the form of its acid halide with the tryptamine in the presence of a hydrogen halide acceptor. Hydrogen halide acceptors which can be used include a tertiary amine, such as pyridine, triethylamine, and the like; alkylene oxides, such as propylene oxide, and the like; urea and substituted ureas, such as N-methylurea, and the like; and inorganic bases, such as sodium bicarbonate, potassium bicarbonate, sodium carbonate, sodium bisulfite, and the like.

The substituted tryptamines used as starting materials in the aforedescribed acylation are prepared by a variety of known procedures. A preparation of 5-methoxy-6-halotryptamines is illustrated by the following generalized reaction scheme:

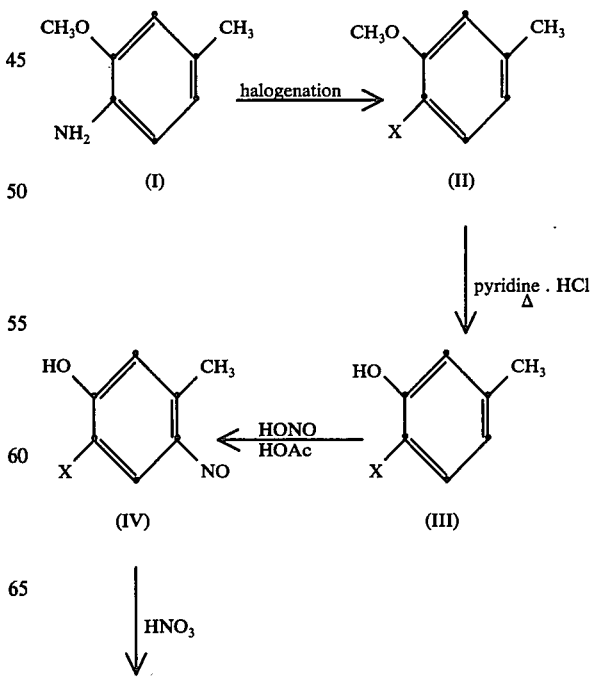

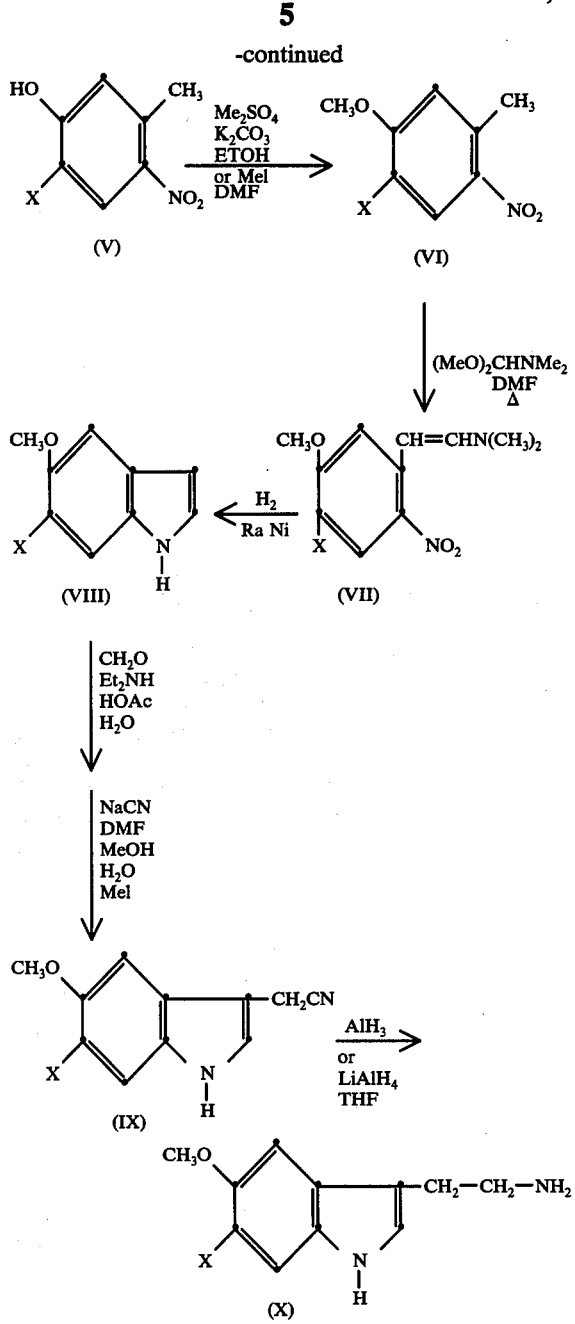

carbonate in methanol or ethanol, or by heating it with methyl iodide and potassium carbonate in N,N-dimethylformamide, to provide 2-nitro-4-halo-5-methoxytoluene (VI). The nitrotoluene compound is reacted with N,N-dimethylformamide dimethylacetal in N,N-dimethylformamide at a temperature of from about 100° C. to about 130° C. to give an N,N-dimethyl-2-(2'-nitro-4'-halo-5'-methoxyphenyl)ethyleneamine intermediate (VII), which, upon hydrogenation over Raney nickel, cyclizes to give a 5-methoxy-6-haloindole (VIII).

The haloindole then is treated with diethylamine and formalin in aqueous acetic acid solution. The resulting mixture is added to aqueous base, and the total is extracted. The solvents are evaporated, and the recovered intermediate product is dissolved in a mixture of water, methanol and N,N-dimethylformamide and is reacted with sodium cyanide. Methyl iodide then is added dropwise to the solution to give a 3-cyanomethyl-5-methoxy-6-haloindole (IX). The cyano compound is reduced with a metal hydride, for example, lithium aluminum hydride, to provide the desired 5-methoxy-6-halotryptaine (X).

Tryptamines having a substitutent at the 2-position of the indole moiety are prepared by a modification of the aforedescribed sequence. Compound VII, prepared as described above, is treated with a compound of the formula

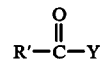

in which Y is halo and R' is $C_1$-$C_4$ alkyl, phenyl or substituted phenyl as aforedescribed. This reaction is carried out in the presence of triethylamine or pyridine and at room temperature to produce the corresponding 2-acyl substituted ethyleneamine (XI). The ethyleneamine then is treated with hydrochloric acid in aqueous dioxane at a temperature of about 100° C. to produce the corresponding 2-nitro-4-halo-5-methoxybenzyl ketone (XII). The latter is ring-closed by treatment with hydrogen over Raney nickel at a temperature of about 25° C. to about 40° C. to the desired 2-substituted indole (XIII). This sequence is illustrated by the following generalized reaction scheme:

As shown in the above generalized reaction scheme, the 5-methoxy-6-halotryptamines are prepared by first halogenating 3-methoxy-4-aminotoluene (I) to give 3-methoxy-4-halotoluene (II). The halogenated compound then is reacted with pyridine hydrochloride at an elevated temperature in the range of from about 180° C. to about 240° C. to provide a 2-halo-5-methylphenol (III). The phenol is reacted with sodium nitrite in acid solution at a temperature from about 0° C. to about 20° C. to give an intermediate nitroso compound (IV). Reaction of the nitroso compound with aqueous nitric acid at a temperature in the range of from about 30° C. to about 60° C. provides a 2-halo-4-nitro-5-methylphenol (V). In those cases in which X is chloro, the 2-chlorophenol intermediate compound is commercially available and thus may itself be used as the initial starting material.

The halonitrophenol then is alkylated, for example, by refluxing it with dimethyl sulfate and potassium

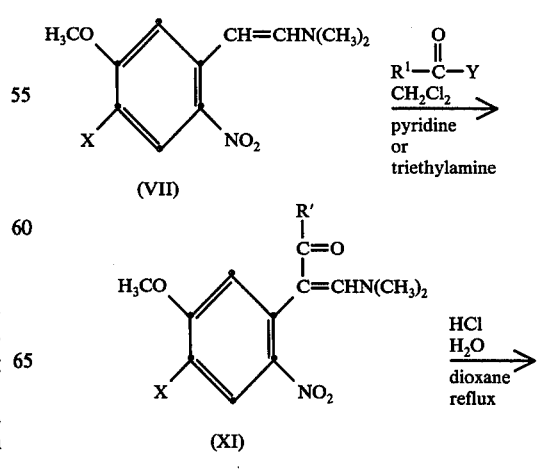

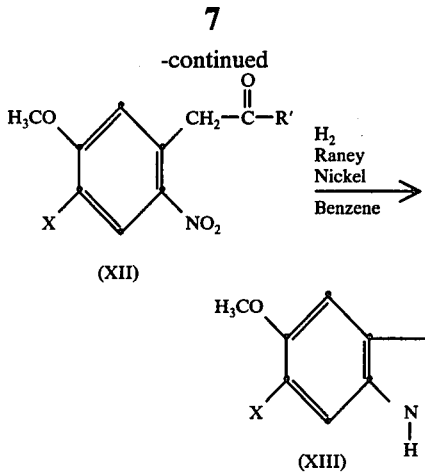

(XII)

(XIII)

Compound XIII then is treated in the manner aforedescribed with reference to compound VIII to produce the desired tryptamine.

Alternatively, the indole, whether unsubstituted at the 2-position (compound VIII) or substituted at the 2-position (compound XIII), can be treated by the following generalized scheme to produce the desire tryptamine intermediate:

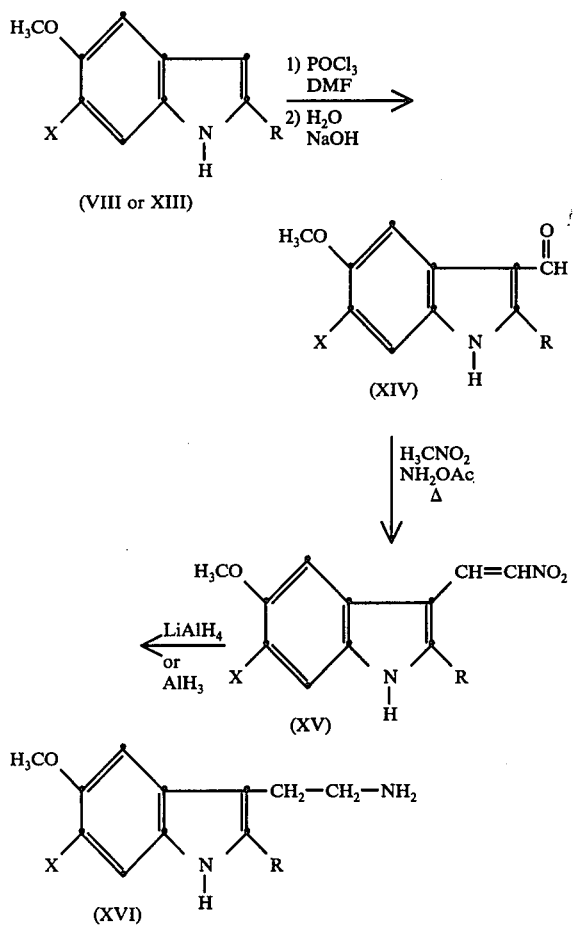

As shown by the above generalized scheme, the indole is treated with phosphorus oxychloride and DMF to produce the corresponding 3-formyl indole (XIV). The latter is treated with nitromethane and ammonium acetate to obtain the corresponding 3-(2'-nitroethenyl)indole (XV), which then is reduced to the desired tryptamine (XVI).

Compounds of this invention in which $R_2$ is other than hydrogen are prepared from the N-unacylated compounds of this invention. They are prepared by treating the latter with an appropriate acylating agent. Typically, the N-unacylated compound is reacted with at least an equimolar amount of an acyl halide of the formula $R_2Cl$ in which $R_2$ represents any of the groups defined above other than hydrogen. The reaction is carried out in the presence of a moderate molar excess (about 10%) of a strong base such as sodium hydride at room temperature in an inert solvent and for a time sufficient to accomplish conversion.

The compounds of this invention exhibit an inhibitory effect on ovulation when administered orally. This inhibitory effect is markedly superior to the effect achieved by oral administration of melatonin. Thus, the compounds of this invention are especially useful as orally active inhibitors of ovulation in birds and mammals. As a result, therefore, the compounds of this invention thus are useful in controlling the animal population and as contraceptives in living beings. The compounds of this invention also are valuable for animal pest control. For example, the compounds of this invention can be formulated in combination with baits and/or attractants and placed in feeding stations accessible to undesirable rodents and other small animals including Canidae such as coyotes, foxes, wolves, jackals, and wild dogs; and birds, such as starlings, galls, redwing blackbirds, pigeons, and the like, to greatly reduce the population thereof. By reason of the activity of the compounds of this invention, they can be used to reduce hazards to aviation by lessening the presence of birds and animals on runways and in the vicinity of air fields. The compounds of this invention also can be used to reduce the population of undesirable birds and animals so as to aid in the prevention and the spread of disease, and to reduce the destruction of property in both rural and urban areas.

The compounds of this invention can be administered as such, or they can be compounded and formulated into pharmaceutical preparations in unit dosage form for oral or parenteral administration. In the compounding or formulation, organic or inorganic solids and/or liquids which are pharmaceutically acceptable carriers can be employed. Suitable such carriers will be well recognized by those of ordinary skill in the art. The compositions may take the form of tablets, powder granules, capsules, suspensions, solutions, and the like.

The compounds of this invention, when administered in an effective amount, will produce the inhibition of pregnancy in birds and mammals. The usual daily dose is from about 0.02 milligrams to about 20 milligrams per kilogram body weight of the recipient. The preferred daily dose is from about 1 milligram to about 8 milligrams per kilogram body weight of the recipient.

The following examples are provided to further illustrate this invention. They are not intended to be limiting upon the scope thereof.

EXAMPLE 1

N-[2-(5-Methoxy-6-chloroindol-3-yl)ethyl]acetamide

A mixture of 142 g. (1.10 mole) of 2-chloro-5-methylphenol in 300 ml. of acetic acid and 40 ml. of sulfuric acid was prepared. The mixture was stirred, and a solution of 70 g. of sodium nitrite in 200 ml. of water was added dropwise over a period of about 100 minutes. During the sodium nitrite addition the temperature of the mixture was maintained at 8°-12° C. with an ice-salt bath. After the addition was completed, the mixture was stirred for another 30 minutes and then was poured into a large volume of ice water. The crude 2-chloro-4-nitroso-5-methylphenol was collected by filtration and used without further purification.

The crude nitroso compound was added in portions to a stirred solution of 100 ml. of 70% nitric acid and 300 ml. of water maintained at a temperature of about 40°-50° C. Heating and stirring were continued until the evolution of brown fumes ceased. The mixture was then poured into water, and the product was collected by filtration. The product was recrystallized from ethanol-water. After collecting the first crop, the mother liquor was concentrated and chilled to yield a second crop of product. Total yield was 155 g. (83%) of 2-chloro-4-nitro-5-methylphenol, m.p. 142°-4° C.

A mixture of 25 g. (0.133 mole) of the 2-chloro-4-nitro-5-methylphenol, 20 g. (0.145 mole) of potassium carbonate, and 14 ml. (18.6 g.; 0.148 mole) of dimethyl sulfate in 500 ml. of absolute ethanol was refluxed for two hours. An additional 19 g. of potassium carbonate and 5 ml. of dimethyl sulfate were added to the mixture, and refluxing was continued for 2 hours. After cooling, the mixture was poured into one liter of cold water and extracted with several portions of ether. The ether extracts were combined, mixed with methylene chloride, and washed with water. The extracts then were dried over sodium sulfate, and the solvents were removed in vacuo. The residue was washed with petroleum ether and dried to yield 26.4 g. (94 percent) of 2-nitro-4-chloro-5-methoxytoluene.

A solution of 15.1 g. (0.075 mole) of the 2-nitro-4-chloro-5-methoxytoluene, 10.7 g. (0.09 mole) of N,N-dimethylformamide-dimethylacetal, and 1.0 g. of triethylenediamine in 100 ml. of N,N-dimethylformamide was heated overnight at about 120° C. in a distillation apparatus under a gentle nitrogen sweep to yield N,N-dimethyl-2-(2'-nitro-4'-chloro-5'-methoxyphenyl)ethyleneamine. The intermediate was not isolated. Instead, it was hydrogenated in situ over 0.4 g. of Raney nickel at 15 psi during which time the temperature rose to 40°-50° C. The hydrogenated solution was filtered, and the filtrate was poured into 500 ml. of ice water containing 10 ml. of acetic acid. The resulting mixture was extracted with several portions of methylene chloride. The combined organic extracts were washed with sodium chloride solution and dried over sodium sulfate. The solvent was removed, and the crude product was sublimed a 4 mm. pressure and 130° C. The colorless sublimate was recrystallized from methanol-water to yield 6.1 g. (45 percent) of 5-methoxy-6-chloroindole, m.p. 126°-28° C.

A solution of 14 ml. of 60 percent acetic acid and 4.8 g. of diethylamine was prepared and cooled to about 5° C. To this solution were added 5.1 ml. of formalin. After stirring for 10 minutes, the cold solution was added to a cold solution of 10 g. (55 mmole) of 5-methoxy-6-chloroindole in 20 ml. of absolute ethanol. The solution was allowed to warm to room temperature and was stirred for one hour. The solution then was poured into 200 ml. of cold 1N sodium hydroxide, and the mixture was extracted several times with ether. The combined ether extracts were washed with sodium chloride solution, dried over sodium sulfate, and the solvent removed in vacuo.

The residue was taken up in a solution of 200 ml. of methanol, 10 ml. of N,N-dimethylformamide, 10 ml. of water and 13.3 g. (0.27 mole) of sodium cyanide. To this solution were added dropwise over a period of about 1 hour 21 ml. (48 g., 0.34 mole) of methyl iodide. After the addition of methyl iodide solution was stirred for about one hour and then was poured into ice water. The aqueous mixture then was extracted with methylene chloride. The extract was dried over sodium sulfate, and the solvent was removed in vacuo. The residue was recrystallized from an ether-pentane mixture to yield 6.1 g. (50 percent) of 3-cyanomethyl-5-methoxy-6-chloroindole, m.p. 133°-137° C.

A solution 7.6 g. (0.2 mole) of lithium aluminum hydride in 200 ml. of tetrahydrofuran was stirred under nitrogen while a solution of 5.2 ml. (9.8 g., 0.1 mole) of 100 percent sulfuric acid in 40 ml. of tetrahydrofuran was added. A solution of 6.0 g. (27 mmoles) of 3-cyanomethyl-5-methoxy-6-chloroindole in 40 ml. of tetrahydrofuran then was added over a 30-minute period. The reaction was allowed to proceed for another hour with stirring. The mixture then was poured into ice followed by 20 percent sodium hydroxide solution. The resulting mixture was extracted with several portions of chloroform. The extracts were washed with sodium chloride solution, dried over sodium sulfate, and the solvent was removed in vacuo. The residue was boiled in ether, and a small amount of pentane was added. The mixture was cooled, and the crystalline product collected by filtration. After drying, 5.04 g. (83 percent) of 5-methoxy-6-chlorotryptamine were obtained.

To a solution of 0.5 g. (2.23 mmoles) of the tryptamine in 5 ml. of pyridine was added 0.5 ml. of acetic anhydride. The mixture was allowed to stand overnight. The solvent was removed in vacuo, and the residue was taken up in a mixture of chloroform and ethyl acetate. The solution was washed with sodium bicarbonate solution and dried over sodium sulfate. The solvent was removed in vacuo. The residue was boiled in benzene. After cooling the product was collected, and the benzene treatment was repeated. The product then was dried to yield 0.52 g. (87 percent) of N-[2-(5-methoxy-6-chloroindol-3-yl)ethyl]acetamide, m.p. 149.5°-150° C.

EXAMPLE 2

N-[2-(5-Methoxy-6-chloroindol-3-yl)ethyl]propionamide

A solution of 0.5 g. (2.23 mmole) of 5-methoxy-6-chlorotryptamine, prepared as described in Example 1, in 4 ml. of benzene and 1 ml. of pyridine was acylated with propionic anhydride following the procedure described in Example 1. N-[2-(5-Methoxy-6-chloroindol-3-yl)ethyl]propionamide, 0.56 g., m.p. 100°-101° C., was obtained.

EXAMPLE 3

N-[2-(5-Methoxy-6-chloroindol-3-yl)ethyl]butyramide

A solution of 0.5 g. (2.23 mmole) of 5-methoxy-6-chlorotryptamine, prepared as described in Example 1, in 5 ml. of pyridine was acylated with butyryl chloride following the procedure described in Example 1. N-[2-(5-Methoxy-6-chloroindol-3-yl)ethyl]butyramide, 0.41 g. (62 percent), m.p. 98°-98.5° C., was obtained.

EXAMPLE 4

N-[2-(5-Methoxy-6-fluoroindol-3-yl)ethyl]acetamide

To 68.5 grams (0.5 mole) of 2-methoxy-4-methylaniline in a 2 liter flask was added a solution of 136 ml. of concentrated hydrochloric acid in 930 ml. of water. The solution was cooled and stirred at about −5° C., and a solution of 42 grams (0.61 mole) of sodium nitrite in 110 ml. of water was slowly added. The mixture was maintained at about −5° C. for about 20 minutes after which 75 ml. (0.60 mole) of 65 percent aqueous hexafluorophosphoric acid were rapidly added. The resulting mixture was stirred and maintained cold for about 30 minutes, and the resulting product then was collected by filtration. The product was washed with 400 ml. of cold water followed by a solution of 120 ml. of methanol and 460 ml. of ether. The resulting diazonium hexafluorophosphate salt was collected on a filter and dried in vacuo overnight. The resulting dried salt weighed 155 grams (96 percent).

A 1 liter flask containing 500 ml. of mineral oil was fitted with a reflux condenser, a magnetic stirrer, a thermometer, and a connecting tube leading to a 300 ml. Erlenmeyer flask. To the Erlenmeyer flask was added the entire quantity of the diazonium salt. The oil was heated to 165° C. by means of an oil bath. The diazonium salt then was added in portions over a 45 minute period. There was a slightly exothermic reaction. Upon completion of the reaction, the flask was rapidly cooled and 400 ml. of 10 percent aqueous sodium carbonate solution were cautiously added. The mixture was subjected to steam distillation. The resulting oily layer was collected. The aqueous layer was extracted with 350 ml. portions of methylene chloride. The methylene chloride extracts were added to the oil, and the entire mixture was dried over sodium sulfate. The solvent was removed in vacuo, and the product was distilled to obtain 34.2 grams of 3-methoxy-4-fluorotoluene, b.p. $_{30\ mm.}$ 93°–95° C.

To a 500 ml. flask were added 200 grams of pyridine hydrochloride. The flask was fitted with a magnetic stirrer, a reflux condenser, and a nitrogen bubbler. The pyridine salt was heated to about 180° C. to remove any moisture. The salt then was allowed to cool somewhat, and 34 grams (0.243 mole) of the fluorotoluene compound were added. The mixture was heated to 220° C. and maintained there for about 3 hours. The mixture then was cooled, and a large volume of water was added. The reaction mixture then was extracted with several portions of methylene chloride. The methylene chloride extracts were combined, and the solvent was removed in vacuo to obtain a pale yellow product which by nmr analysis indicated the presence of about 5 percent of starting material. The product then was taken up in an excess of 1M sodium hydroxide. The solution was extracted with methylene chloride, and the aqueous layer then was acidified with hydrochloric acid. The acidified portion was extracted with methylene chloride. Evaporation of the methylene chloride extract and distillation of the residue gave 26.6 grams of 2-fluoro-5-methylphenol, b.p.$_{30}$ 86°–93° C.

A solution of 26.6 grams (0.21 mole) of the fluorophenol in 63 ml. of acetic acid and 8.5 ml. of sulfuric acid was stirred at 8°–12° C. While the mixtute was cooled and stirred, a solution of 15 grams of sodium nitrite in 42 ml. of water was added dropwise over a period of about 1 hour. Stirring was continued for an additional 30 minutes. The mixture then was poured into a large volume of ice water. The resulting crude product was collected by filtration, thoroughly washed with water, and air dried while on the filter. The resulting crude nitroso compound then was added in portions to a stirred solution of 20 ml. of 70 percent nitric acid and 60 ml. of water maintained at 40°–50° C. Heating and stirring were continued until the evolution of brown fumes became negligible. The mixture then was poured into ice water, and the crude product was collected. The crude product then was recrystallized from ethanol-water to obtain a first and a second crop. A total of 25.4 grams (70 percent) of 2-fluoro-4-nitro-5-methylphenol was obtained, m.p. 110°–111.5° C.

A mixture of 25 grams (0.15 mole) of the fluoronitrophenol, 22 grams of potassium carbonate, 15.4 ml. of dimethyl sulfate, and 550 ml. of ethanol was refluxed overnight. Analysis of the reaction mixture indicated that no alkylation had taken place. The mixture then was diluted with 300 ml. of N,N-dimethylformamide and about 50 ml. of water. Two equivalents of methyl iodide then were added. The mixture was heated at 100° C. overnight. The mixture then was cooled and added to a large volume of ice water. The product separated, was collected by filtration, and dried. The collected product was recrystallized from methanol-water to obtain 22.2 grams of 2-nitro-4-fluoro-5-methoxytoluene, m.p. 95°–95.5° C.

A mixture of 10 grams (0.054 mole) of the fluoronitrotoluene, 7.7 grams (0.065 mole) of N,N-dimethylformamide dimethylacetal, and 1.0 grams of triethylenediamine in 75 ml. of N,N-dimethylformamide was heated at 125° C. under a gentle nitrogen sweep overnight. The solvent then was removed in vacuo with gentle application of heat. The resulting residue was taken up in methanol and filtered to give a deep red-green irridescent product, m.p. 116°–117° C. A total of 8.35 grams (64 percent) of N,N-dimethyl-2-(2'-nitro-4'-fluoro-5'-methoxyphenyl)ethyleneamine was obtained.

The ethyleneamine was hydrogenated in benzene over Raney nickel. The resulting reaction mixture was washed with 500 ml. of water containing 4 ml. of phosphoric acid. The resulting aqueous phase then was extracted with methylene chloride, and all the organic portions were combined. The combined organic solutions then were washed with aqueous sodium chloride solution and dried over sodium sulfate. The solvent then was removed in vacuo, and the resulting crude product was sublimed from a fused state at 0.2 mm. pressure. The resulting sublimate was recrystallized from methanol-water to obtain a first and second crop totalling 3.02 grams (54 percent) of 5-methoxy-6-fluoroindole, m.p. 73°–74° C.

To a mixture of 2.8 ml. of 60 percent acetic acid and 0.96 grams of diethylamine maintained at about 5° C. was added 1.0 ml. of formalin. The resulting solution was added to a mixture of 2.0 grams (12.1 mmole) of the fluoroindole in 4 ml. of absolute ethanol. The solution was allowed to warm to room temperature and was stirred for about 1 hour. The solution then was poured into 40 ml. of 1N sodium hydroxide. The resulting mixture was extracted several times with ether. The ether extracts were combined and washed with aqueous sodium chloride solution, dried over sodium sulfate, and evaporated. The resulting residue was added to a solution of 40 ml. of methanol, 2 ml. of N,N-dimethylformamide, 2 ml. of water, and 2.66 grams of sodium cyanide. To the resulting mixture then were added dropwise 4.2 ml. (9.6 grams; 0.068 mole) of methyl iodide over a period of about 1 hour. The resulting mixture was maintained for about another hour. The mixture then was poured into ice water, and the aqueous mixture was extracted with methylene chloride. The extract was dried over sodium sulfate, and the solvent was removed in vacuo. The residual product then was washed with a cold mixture of ether and petroleum ether. The product was recrystallized from benzene-hexane to obtain 1.11 grams (45 percent) of 3-cyanomethyl-5-methoxy-6-fluoroindole, m.p. 97°–98° C.

A solution of 1.9 grams (0.05 mole) of lithium aluminum hydride in 50 ml. of tetrahydrofuran was prepared and stirred under nitrogen. A solution of 1.3 ml. (2.45 grams; 0.025 mole) of 100 percent sulfuric acid in 10 ml. of tetrahydrofuran was prepared and then was added to the lithium aluminum hydride solution. The resulting mixture contained lithium sulfate as a suspension. A solution of 1.0 grams (4.9 mmole) of the cyanomethylindole in 10 ml. of tetrahydrofuran then was added to the mixture over a period of about 15 minutes. Stirring was continued for an additional 1 hour. The reaction mixture then was poured into ice followed by 20 percent sodium hydroxide solution. The resulting mixture was extracted with several portions of chloroform. The extracts were washed with sodium chloride solution, dried over sodium sulfate, and the solvent was removed in vacuo. The resulting residual oil crystallized upon addition of ether. The tan product was washed three times with small amounts of a 1:1 mixture of ether and petroleum ether. Upon drying, 0.83 grams (81 percent) of 5-methoxy-6-fluorotryptamine was obtained. m.p. 114°–117° C. Recrystallized from benzene-hexane, m.p. 120°–121° C.

A mixture of 0.75 grams (3.6 mmole) of the tryptamine, 2.0 ml. of pyridine, and 8.0 ml. of benzene was prepared. Acetic anhydride (1.0 ml.) was slowly added. The mixture was stirred at room temperature for 4 hours, and the solvents then were removed in vacuo with moderate heating. The resulting crystalline residue was dissolved in a 1:1 mixture of warm ethyl acetate and chloroform. The solution was washed with water, then with sodium chloride solution, and then dried over sodium sulfate. The solvents were removed in vacuo. The crystalline residue was boiled in benzene for a few minutes. The mixture was allowed to stand at room temperature for several hours, and the resulting product was collected by filtration and dried to obtain 0.81 grams (90 percent) of N-[2-(5-methoxy-6-fluoroindol-3-yl)ethyl]acetamide, m.p. 158°–159° C.

EXAMPLE 5

N-[2-(6-Chloro-5-methoxy-2-methylindol-3-yl)ethyl]-acetamide

To a solution of 20 g. (0.078 mole) of N,N-dimethyl-2-(2'-nitro-4'-chloro-5'-methoxyphenyl)ethyleneamine and 19.8 ml. (19.4 g., 0.25 mole) of pyridine in 200 ml. of methylene chloride was added dropwise a solution of 11 ml. (12.2 g., 0.156 mole) of acetyl chloride in 200 ml. of methylene chloride. The addition was carried out over a period of about 3 hours. The mixture was stirred overnight and then was poured into a large volume of cold NaHCO$_3$ solution. The aqueous phase was extracted with fresh methylene chloride. The combined organic solutions were washed with water and dried over sodium sulfate. Removal of the solvent in vacuo gave a residue which was dissolved in 450 ml. of dioxane. To the resulting solution were added 150 ml. of 1M HCl solution. After stirring overnight at room temperature, the solution was refluxed for 3 days. After cooling, 80 ml. of 1M NaOH were added, and the bulk of the dioxane was removed under reduced pressure. The product was then extracted into chloroform. The extract was evaporated, and the residue was chromatographed over 200 g. of florosil, eluting with benzene. Crystallization from benzene-hexane gave 6.49 g. (34% yield) of 4-chloro-5-methoxy-2-nitrophenylacetone, m.p. 114°–115° C.

Using 2 g. of Raney nickel, 6.49 g. (0.026 mole) of the arylacetone in 90 ml. of benzene were hydrogenated under 50 psi of hydrogen for 1 hour. The exothermic reduction caused the temperature to rise to 40° C. After removal of the benzene, the residue was crystallized from methanol-water affording 1.5 g. of 6-chloro-5-methoxy-2-methylindole, m.p. 115°–116° C. Evaporation of the mother liquor followed by sublimation and recrystallization from methanol-water provided another 0.62 g. of product, m.p. 114°–115° C. Total yield: 2.12 g., 41%.

A mixture of 3.6 ml. (3.42 g. 0.047 mole) of DMF and 1.04 ml. (1.74 g., 0.0114 mole) of phosphorus oxychloride was prepared at 10°–20° C. After 15 minutes, 2.05 g. (0.0105 mole) of the indole in 1 ml. of DMF was added, and the temperature was raised to 35° C. After 1 hour the mixture was poured onto crushed ice. This mixture was treated gradually with 2 g. of NaOH in 10 ml. of water, maintaining an acidic pH through the first three-fourths of the addition. Following addition of the base, the mixture was boiled for one hour. After the mixture was cooled and allowed to stand overnight, the product was collected. Boiling the product in methanol afforded 2.13 g. (91% yield) of pure 6-chloro-5-methoxy-2-methylindole-3-carboxaldehyde, m.p. 256° dec.

A mixture of 0.5 g. (0.002 mole) of the indolecarboxaldehyde, 40 ml. of nitromethane, 10 drops of acetic acid, and 0.4 g. of ammonium acetate was refluxed overnight. Another 0.4 g. of ammonium acetate was added, and the mixture was refluxed for an additional day. The nitromethane was removed in vacuo, and the residue was washed with water. Recrystallization from ethanol gave 0.35 g. (59% yield) of pure 1-(6'-chloro-5'-methoxy-2'-methylindol-3'-yl)-2-nitroethene, m.p. 238° dec.

A solution of 1.47 g. (0.039 mole) of lithium aluminum hydride in 90 ml. of THF was stirred under nitrogen. A solution of 1.02 ml. of sulfuric acid (100%) in 15 ml. of THF was added to the mixture followed by addition over a one hour period of a solution of 0.35 g. (0.0013 mole) of the nitrovinylindole in 15 ml. of THF. The mixture was stirred overnight, and the excess hydride then was destroyed by addition of ice chips. The mixture then was poured into a 20% NaOH solution, and the total was extracted with several portions of chloroform. After drying over sodium sulfate, the solvent was removed from the extracts, and the residue was recrystallized from benzene-hexane. The yield of 6-chloro-5-methoxy-2-methyltryptamine, m.p. 152°–153° C; was 0.50 g. (79%).

A solution of 0.11 g. of the tryptamine in 5 ml. of benzene and 0.37 ml. of pyridine was stirred in an ice bath. To the stirred mixture was added 0.05 ml. of acetic anhydride. After stirring for 1 hour at room temperature, the mixture was poured into ice water and extracted with benzene. The benzene extract was dried over sodium sulfate and evaporated in vacuo. The residue was chromatographed over 10 g. of silica gel eluting with ethyl acetate. The pure N-[2-(6-chloro-5-methoxy-2-methylindol-3-yl)ethyl]-acetamide, m.p. 119°–121° C; weighing 0.11 g. (85% yield) was recovered.

EXAMPLE 6

N-[2-(1-Acetyl-5-methoxy-6-chloroindol-3-yl)ethyl]-acetamide.

To 30 ml. of N,N-dimethylformamide were added 210.7 mg. (0.79 mmole) of N-[2-(5-methoxy-6-chloroindol-3-yl)ethyl]acetamide (prepared as in Example 1) followed by 20.8 mg. of sodium hydride. The resulting mixture was stirred at room temperature for about one hour, and 68.2 mg. (0.06 ml.) of acetyl chloride were added. The mixture was stirred for an additional hour and then was poured into ice water containing a small amount of acetic acid. The resulting mixture was extracted with chloroform, and the extract was washed twice with saturation aqueous sodium chloride solution. The chloroform extract was dried over sodium sulfate and was concentrated in a rotary evaporator. The residue was recrystallized from benzene-ether and was vacuum-dried to obtain 108 mg. (40.8%) of the title compound, m.p. 178°–181° C.

Analysis, Calc'd for $C_{15}H_{17}N_2O_3Cl$: C, 58.35; H, 5.55; N, 9.07. Found: C, 58.02*; H, 5.82*; N, 9.07.*
*Result is an average of two analyses.

IR (KBr) 1646 (C=O), 1703 cm$^{-1}$ (C=O). UV $\lambda_{max}$ (MeOH) 256 ($\epsilon$ 17,200), 274 sh nm ($\epsilon$ 10,300). NMR (DMSO-d$_6$) $\delta$ 1.81 (s, 3H, amide Ac); 2.29 (t, J=7 Hz., 2H, $\alpha$-CH$_2$); 2.58 (s, 3H, 1-Ac); 3.37 (q, J=7 Hz, 2H, $\beta$-CH$_2$); 3.90 (s, 3H, OCH$_3$); 7.33 (s, 1H, 4-H); 7.67 (s, 1H, 2-H); 7.99 (broad t, 1H, N-H); and 8.31 (s, 1H, 7-H).

The following Table is provided to show ovulation inhibitory activity of the compounds of this invention. Adult female rats with regular estrus cycles of four days each are employed. The estrus cycle consists of 2 days of diestrus followed by a day of proestrus and then a day of estrus. On the afternoon of proestrus, luteinizing hormone (LH) is released into the blood by the pituitary gland. The LH travels to the ovary where it induces ovulation, resulting in the presence of eggs in the oviduct on the day of estrus.

The test compound is administered orally at noon on the day of proestrus. The rat is sacrificed on the following day (estrus), and the oviduct is removed and examined microscopically for the presence of ova. The absence of ova indicates that the compound is active in blocking ovulation.

Table
Inhibition of Ovulation

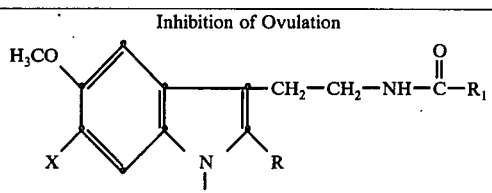

| R | R$_1$ | X | Inhibition Min. Eff. Dose, mg. |
|---|---|---|---|
| H | CH$_3$ | H$^a$ | 8 |
| H | CH$_3$ | Cl | 1 |
| H | C$_2$H$_5$ | Cl | 1 |
| H | C$_3$H$_7$ | Cl | 4 |
| H | CH$_3$ | F | 1 |
| CH$_3$ | CH$_3$ | Cl | 1 |

$^a$Melatonin

We claim:
1. A compound of the formula

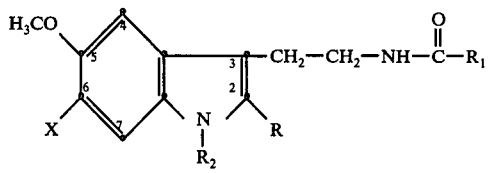

in which
R is hydrogen, C$_1$–C$_4$ alkyl, phenyl, or phenyl substituted with halo, C$_1$–C$_4$ alkyl, or C$_1$–C$_4$ alkoxy;
R$_1$ is hydrogen or C$_1$–C$_4$ alkyl;
R$_2$ is hydrogen, haloacetyl, C$_1$–C$_5$ alkanoyl, benzoyl, or benzoyl substituted with halo or methyl; and
X is halogen.
2. Compound of claim 1, in which R$_2$ is hydrogen.
3. Compound of claim 2, in which R is hydrogen or methyl.
4. Compound of claim 3, in which R is hydrogen.
5. Compound of claim 2, in which R$_1$ is hydrogen.
6. Compound of claim 2, in which R$_1$ is C$_1$–C$_4$ alkyl.
7. Compound of claim 6, in which R$_1$ is methyl.
8. Compound of claim 6, in which R$_1$ is ethyl.
9. Compound of claim 2, in which X is chloro.
10. Compound of claim 2, in which X is fluoro.
11. Compound of claim 1, in which R$_2$ is halo-acetyl, C$_1$–C$_5$ alkanoyl, benzoyl, or benzoyl substituted with halo or methyl.
12. Compound of claim 11, in which R is hydrogen or methyl.
13. Compound of claim 12, in which R is hydrogen.
14. Compound of claim 11, in which R$_1$ is hydrogen.
15. Compound of claim 11, in which R$_1$ is C$_1$–C$_4$ alkyl.
16. Compound of claim 15, in which R$_1$ is methyl.
17. Compound of claim 15, in which R$_1$ is ethyl.
18. Compound of claim 11, in which X is chloro.
19. Compound of claim 11, in which X is fluoro.
20. Compound of claim 18, in which R$_2$ is acetyl.
21. Compound of claim 18, in which R$_2$ is pivaloyl.
22. Compound of claim 18, in which R$_2$ is benzoyl.
23. Compound of claim 18, in which R$_2$ is 4-chlorobenzoyl.
24. Compound of claim 18, in which R$_2$ is 2-methylbenzoyl.
25. Compound of claim 18, in which R$_2$ is 2,6-dimethylbenzoyl or 2,4,6-trimethylbenzoyl.

* * * * *